US011796465B2

(12) United States Patent
Jos et al.

(10) Patent No.: US 11,796,465 B2
(45) Date of Patent: Oct. 24, 2023

(54) METHOD AND SYSTEM FOR PREDICTING BLOOD COMPOUND CONCENTRATION OF A TARGET (71) Applicant: SAMSUNG ELECTRONICS CO., LTD., Suwon-si (KR)

(72) Inventors: Sujit Jos, Bangalore (IN); Kiran Bynam, Bangalore (IN); Ibrahim A, Bangalore (IN); Rahul Arora, Bangalore (IN); Gorish Aggarwal, Bangalore (IN); So Young Lee, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 244 days.

(21) Appl. No.: 17/163,857

(22) Filed: Feb. 1, 2021

(65) Prior Publication Data
US 2021/0247304 A1 Aug. 12, 2021

(30) Foreign Application Priority Data

Feb. 6, 2020 (IN) .............................. 202041005234
Jul. 23, 2020 (KR) ........................ 10-2020-0091730

(51) Int. Cl.
G01N 21/3577 (2014.01)
G01N 21/359 (2014.01)
(Continued)

(52) U.S. Cl.
CPC ....... *G01N 21/3577* (2013.01); *G01N 21/359* (2013.01); *G01N 33/49* (2013.01);
(Continued)

(58) Field of Classification Search
CPC .. G01N 21/3577; G01N 21/359; G01N 33/49; G01N 2210/12; G06N 20/00; G06N 5/04
(Continued)

(56) References Cited

U.S. PATENT DOCUMENTS 7,830,519 B2 11/2010 Mah et al.
9,089,292 B2 7/2015 Roy et al.
(Continued)

FOREIGN PATENT DOCUMENTS

KR 10-2013-0104883 A 9/2013
WO 2017/165693 A1 9/2017

*Primary Examiner* — Michael P Nghiem
(74) *Attorney, Agent, or Firm* — Sughrue Mion, PLLC (57) ABSTRACT A method of predicting a blood compound concentration of a target may include receiving, by a system, spectral data associated with a region of the target, using near-infrared (NIR) spectroscopy. The method may include classifying, by the system, each of the plurality of data instances of the spectral data to one of a plurality of labelled classes. The method may include obtaining, by the system, one or more best fit models from a plurality of prediction models based on the classification. The method may include determining, by the system, blood compound concentration values corresponding to each of the one or more best fit models. The method may include predicting, by the system, the blood compound concentration of the target using the blood compound concentration values predicted using the best fit models.

8 Claims, 5 Drawing Sheets (51) Int. Cl.
*G01N 33/49* (2006.01)
*G06N 5/04* (2023.01)
*G06N 20/00* (2019.01)

(52) U.S. Cl.
CPC ............... *G06N 5/04* (2013.01); *G06N 20/00* (2019.01); *G01N 2201/12* (2013.01)

(58) Field of Classification Search
USPC .......................................................... 702/25
See application file for complete search history.

(56) References Cited

U.S. PATENT DOCUMENTS

| | | |
|---|---|---|
| 9,324,035 B2 | 4/2016 | Lee et al. |
| 9,589,442 B2 | 3/2017 | Barfield, Jr. et al. |
| 9,924,894 B2 | 3/2018 | Zhang et al. |
| 2006/0167350 A1* | 7/2006 | Monfre ................ A61B 5/1455 128/920 |
| 2006/0253296 A1 | 11/2006 | Liisberg et al. |
| 2013/0324861 A1 | 12/2013 | Ando et al. |
| 2015/0220702 A1 | 8/2015 | Hovorka |
| 2018/0192963 A1* | 7/2018 | Budiman ............... A61B 5/002 |
| 2019/0261928 A1* | 8/2019 | Jos ....................... A61B 5/7275 |
| 2020/0197605 A1* | 6/2020 | Haidar ................... G16H 50/20 |
| 2022/0061672 A1* | 3/2022 | Cui ................... A61B 5/14532 |

\* cited by examiner

METHOD AND SYSTEM FOR PREDICTING BLOOD COMPOUND CONCENTRATION OF A TARGET

CROSS-REFERENCE TO RELATED APPLICATION(S)

This application is based on and claims priority under 35 U.S.C. § 119 to Indian Patent Application No. 202041005234, filed on Feb. 6, 2020, in the Indian Patent Office, and to Korean Patent Application No. 10-2020-0091730, filed on Jul. 23, 2020, in the Korean Intellectual Property Office, the disclosures of which are incorporated by reference herein in their entireties.

BACKGROUND

1. Field

The disclosure is related, in general to health monitoring and more particularly, but not exclusively to a method and system for prediction of a blood compound concentration in a test subject.

2. Description of Related Art

Non-invasive techniques for measurement of parameters in a human or animal body have been found to be highly desirable, especially using spectroscopy. Current non-invasive methods for monitoring or measuring metabolic-parameters include polarimetry, mid-infrared spectroscopy, Raman spectroscopy, Kromoscopy, fluorescence spectroscopy, nuclear magnetic resonance spectroscopy, radio-frequency spectroscopy, ultrasound, transdermal measurements, photoacoustic spectroscopy, and so on. Near-infrared (NIR) a spectroscopy is a much explored and a widely preferred method in current research for non-invasive monitoring of glucose values.

Conventional methods transmit the electromagnetic radiation of a wavelength through the skin to the target measurement region and the collected light is analyzed and compared against a stored reference calibration value or curve. The reference calibration value or curve used for predicting glucose concentration values may not be feasible since the calibration value or curve varies from person to person or animal to animal. The values of metabolic parameters thus obtained or predicted may not be accurate. Therefore, there is a need for a method and a system that accurately predicts glucose concentration in blood by selecting a best prediction model.

The information disclosed in this background of the disclosure section is only for enhancement of understanding of the general background of the disclosure and should not be taken as an acknowledgement or any form of suggestion that this information forms the prior art already known to a person skilled in the art.

SUMMARY

Additional aspects will be set forth in part in the description which follows and, in part, will be apparent from the description, or may be learned by practice of the presented embodiments.

According to an aspect of the disclosure, a method of predicting a blood compound concentration of a target may include receiving, by a system, spectral data associated with a region of the target, using near-infrared (NIR) spectroscopy. The method may include classifying, by the system, each of the plurality of data instances of the spectral data to one of a plurality of labelled classes. The method may include obtaining, by the system, one or more best fit models from a plurality of prediction models based on the classification. The method may include determining, by the system, blood compound concentration values corresponding to each of the one or more best fit models. The method may include predicting, by the system, the blood compound concentration of the target using the blood compound concentration values predicted using the best fit models.

According to an aspect of the disclosure, a system for predicting a blood compound concentration of a target includes a processor; and a memory communicatively coupled with the processor. The memory stores processor-executable instructions, which when executed by the processor cause the processor to: receive spectral data associated with a region of the target, using near-infrared (NIR) spectroscopy, wherein the spectral data comprises a plurality of data instances collected at a plurality of time intervals; classify each of the plurality of data instances of the spectral data to one of a plurality of labelled classes, wherein each of the plurality of labelled classes is predetermined using a historical spectral data associated with a plurality of training subjects; obtain one or more best fit models from a plurality of prediction models based on the classification, wherein the plurality of prediction models are models corresponding to the plurality of training subjects; determine blood compound concentration values corresponding to each of the one or more best fit models; and predict the blood compound concentration of the target using the blood compound concentration values predicted using the best fit models.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The above and other aspects, features, and advantages of certain embodiments of the present disclosure will be more apparent from the following description taken in conjunction with the accompanying drawings, in which.

It should be appreciated by those skilled in the art that any block diagrams herein represent conceptual views of illustrative systems embodying the principles of the disclosure. Similarly, it will be appreciated that any flow charts, flow diagrams, state transition diagrams, pseudo code, and the like, represent various processes which may be substantially represented in a computer readable medium and executed by a computer or processor, whether or not such computer or processor is explicitly shown.

DETAILED DESCRIPTION

In the disclosure, the word "exemplary" is used herein to mean "serving as an example, instance, or illustration." Any embodiment or implementation of the disclosure described herein as "exemplary" is not necessarily to be construed as preferred or advantageous over other embodiments.

While the disclosure is susceptible to various modifications and alternative forms, specific embodiments thereof are shown by way of example in the drawings and will be described in detail below. It should be understood, however, that it is not intended to limit the disclosure to the specific forms disclosed, but on the contrary, the disclosure is to cover all modifications, equivalents, and alternatives falling within the scope of the disclosure.

The terms "comprises," "comprising," "includes," or any other variations thereof, are intended to cover a non-exclusive inclusion, such that a setup, device, or method that comprises a list of components or steps might not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The disclosure relates to a method and a blood compound monitoring system (BMS) for predicting blood compound concentration of a test subject. In an embodiment, the test subject may be a human or an animal, whose blood compound concentration value may be predicted by the BMS. In an embodiment, a spectral data associated with a target body region of a test subject may be measured by a spectrometer using NIR spectroscopy. The test subject may be a human or an animal that is subjected to various observations for monitoring and collecting spectral data related to the test subject. The spectral data is measured or collected at a plurality of time intervals as a plurality of data instances. Each of the data instances of the spectral data is classified to one of a plurality of labelled classes. The labelled classes are predetermined using historical spectral data associated with training subjects and historical blood compound concentration values associated with historical spectral data. Based on classification, a predefined number of best fit models are determined from a plurality of prediction models corresponding to training subjects. Using each best fit model, blood compound concentration values are determined. The blood compound concentration of the test subject is then predicted by the blood compound concentration values predicted by the best fit models.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1:
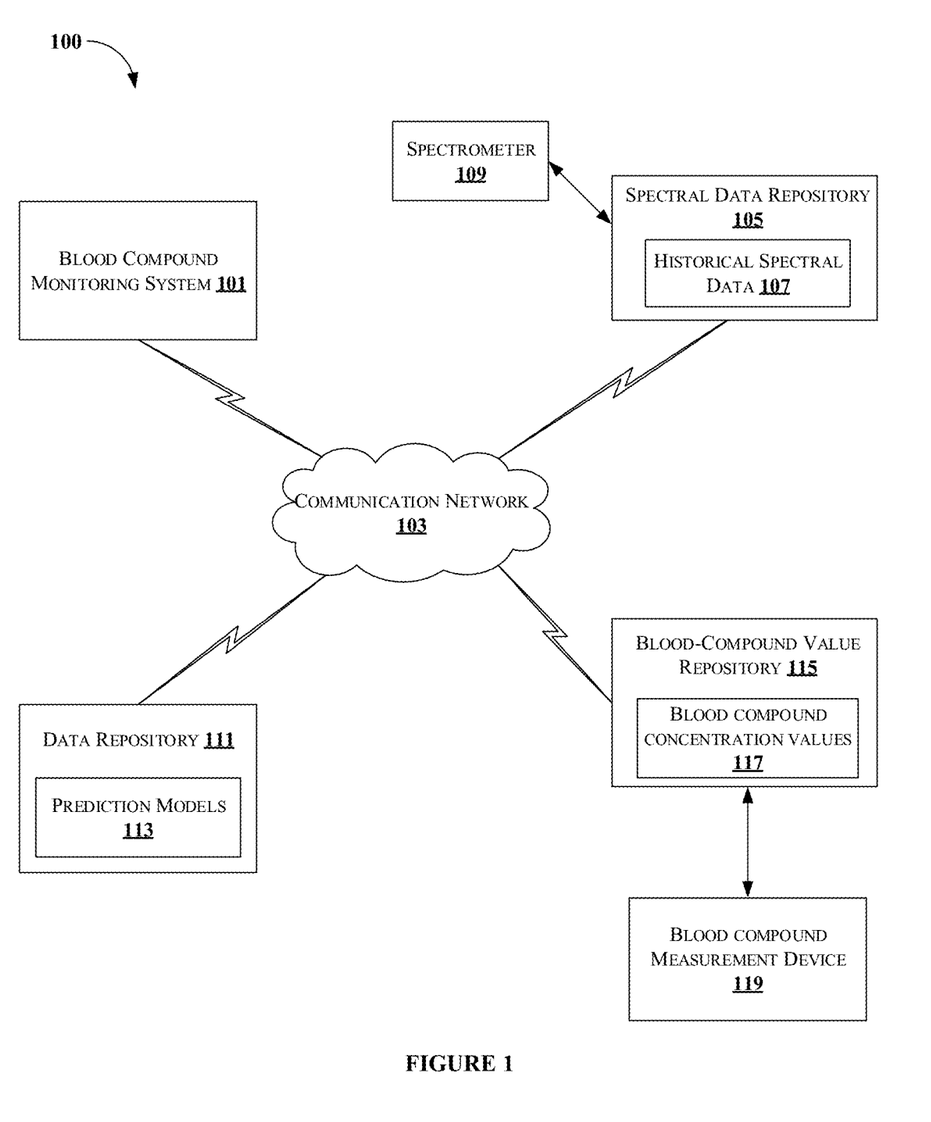
FIG. 1 illustrates an exemplary environment including a system for predicting a blood compound concentration of a target according to an embodiment.

FIG. 1 illustrates an exemplary environment 100 including a blood compound monitoring system 101 for predicting blood compound concentration of a target according to an embodiment.

As illustrated in FIG. 1, the exemplary environment 100 may include a blood compound monitoring system 101 (hereinafter referred to as "BMS 101"), a spectral data repository 105, a blood compound value repository 115, and a data repository 111, each communicatively coupled via a communication network 103. The communication network 103 may include, without limitation, a direct interconnection, Local Area Network (LAN), Wide Area Network (WAN), wireless network (e.g., using Wireless Application Protocol), the Internet, and the like.

In an embodiment, the spectral data repository 105 may be configured to store spectral data 107 associated with a plurality of test subjects. As an example, the historical spectral data 107 may include, without limitation, spectral data measured or collected for various training subjects using NIR spectroscopy. The historical spectral data 107 may be measured by a spectrometer 109. The spectrometer 109 may be any measurement device capable of collecting spectral data 107 from a target body region of test subjects in a specified wavelength range. In an embodiment, the spectral data repository 105 may be integrated with the BMS 101. In another embodiment, the spectral data repository 105 may be configured as a standalone device, independent of the BMS 101.

In an embodiment, the blood compound value repository 115 may store a plurality of historical blood compound concentration values 117 associated with plurality of training subjects. The historical blood compound concentration values 117 may be measured by a blood compound measurement device 119. In an embodiment, the historical blood compound concentration values 117 may be measured for the plurality of training subjects and stored in the blood compound value repository 115. In an alternative embodiment, the blood compound value repository 115 may be integrated with the BMS 101. In another embodiment, the blood compound value repository 115 may be configured as a standalone device, independent of the BMS 101. In yet another embodiment, the spectral data repository 105 and the blood compound value repository 115 may be configured as a single repository that stores all historical data associated with the training subjects and may be coupled with the BMS 101.

In an embodiment, the data repository 111 may store the prediction models 113 associated with the plurality of training subjects. The prediction models 113 are the models that establish the relationship or association between the historical spectral data 107 measured by the spectrometer 109 and the blood compound concentration values 117 measured by the blood compound measurement device 119. In an embodiment, the data repository 111 may be integrated with the BMS 101. In another embodiment, the data repository 111 may be configured as standalone device, independent of the BMS 101. In yet another embodiment, the spectral data repository 105, the blood compound value repository 115 and the data repository 111 may be configured as a single repository, coupled with the BMS 101.

Figure 2A:
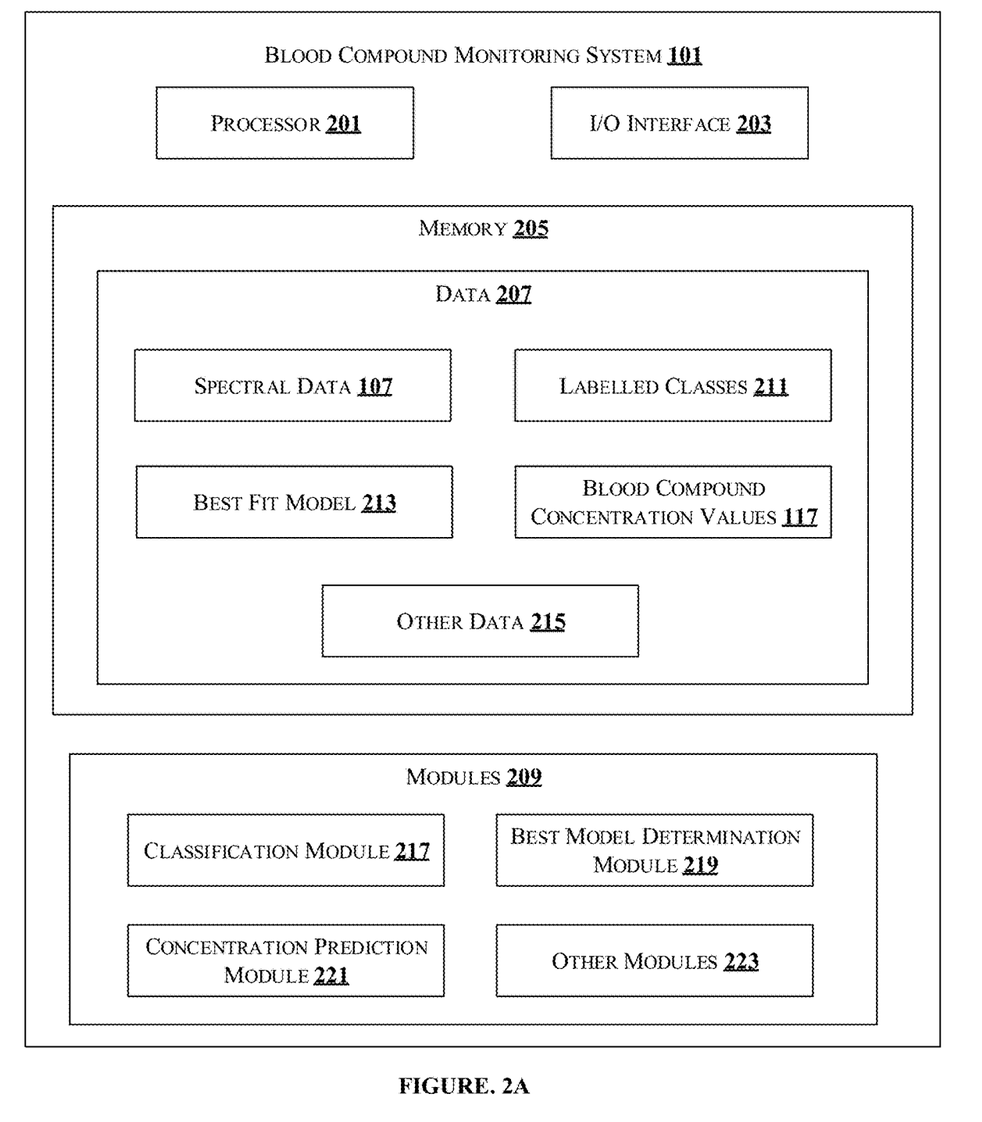
FIG. 2A shows a detailed block diagram of a blood compound monitoring system according to an embodiment.

FIG. 2A shows a detailed block diagram of a blood compound monitoring system 101 according to an embodiment.

In some implementations, the BMS 101 may include a processor 201, an I/O interface 203, and a memory 205. In an embodiment, the I/O interface 203 may be configured to receive historical spectral data 107 from a spectral data repository 105 associated with the BMS 101. Further, the I/O interface 203 may be configured to receive prediction models 113 and blood compound concentration values 117 respectively from a data repository 111 and a blood compound value repository 115, associated with the BMS 101. The memory 205 may be communicatively coupled to the processor 201, and may store data 207 and one or more modules 209. The processor 201 may be configured to perform various functionalities of the BMS 101, using the data 207 and the one or more modules 209.

In an embodiment, the data 207 may include, without limitation, spectral data 107, labelled classes 211, best fit model 213, blood compound concentration values 117, and other data 215. In some implementations, the data 207 may be stored within the memory 205 in the form of various data structures. Additionally, the data 207 may be organized using data models, such as relational or hierarchical data models. In an embodiment, the other data 215 may store various temporary data and files generated by the one or more modules 209 while performing various functions of the BMS 101. As an example, the other data 215 may also include, without limitation, a plurality of prediction models 113, current and historical spectral data 107 of the subjects, and the like.

In some embodiments, the data stored in the memory 205 may be processed by the modules of the BMS 101. In an embodiment, the modules may be stored within the memory 205. In an alternative embodiment, the modules may also be present outside the memory 205 and may be communicatively coupled to the processor 201 as independent hardware components. As used herein, the term modules may refer to an Application Specific Integrated Circuit (ASIC), an electronic circuit, a processor (shared, dedicated, or group) and the like, which execute one or more software or firmware programs, a combinational logic circuit, and/or other suitable components that provide the described functionality.

In some embodiments, the modules 209 may include, for example, a classification module 217, a best model determination module 219, a concentration prediction module 221 and other modules 223. In an embodiment, the other modules 223 may be used to perform various miscellaneous functionalities of the BMS 101. It will be appreciated that such aforementioned modules 209 may be represented as a single module or a combination of different modules.

Furthermore, a person of ordinary skill in the art will appreciate that, in an implementation, the one or more modules 209 may be stored in the memory 205, without limiting the scope of the disclosure.

In an embodiment, the classification module 217 may be configured to classify each of the plurality of data instances of the spectral data 107 of the test subject into one of a plurality of labelled classes 211. As an example, the plurality of data instances may correspond to values of the spectral data 107 collected at a plurality of time intervals. Further, each of the plurality of labelled classes may correspond to and represent one of the plurality of training subjects.

In an embodiment, the best model determination module 219 may be configured to determine one or more best fit models 213 from a plurality of prediction models 113 based on the classification. In an embodiment, the best fit model 213 may be a prediction model having labelled classes with highest count of data instances.

In an embodiment, the concentration prediction module 221 may be configured for calculating blood compound concentration values 117 for each of the plurality of best fit models 213. Further, the concentration prediction module 221 may also be configured for determining the blood compound concentration of the test subject using the calculated blood compound concentration values 117.

In operation, the spectrometer 109 associated with the BMS 101 may capture spectral data 107 associated with a target body region of the test subject using NIR spectroscopy. In an embodiment, the spectral data 107 may include, without limitation, a plurality of data instances collected at plurality of time intervals. Once the spectral data 107 is collected, it may be transmitted to the BMS 101. The BMS 101 may process and classify the spectral data 107 into one of the plurality of labelled classes 211 using the classification module 217. As an example, the plurality of labelled classes 211 may correspond to the plurality of training subjects and may be the multi-class classifier outputs. In an embodiment, the plurality of labelled classes 211 may be predetermined using the historical spectral data 107 associated with the plurality of training subjects. In an implementation, the historical spectral data 107 and a plurality of historical blood compound values for the plurality of subjects may be obtained from the spectral data repository 105 and the blood compound value repository 115 associated with the BMS 101.

In an embodiment, the classification module 217, upon receiving the plurality of data instances of the spectral data 107, may classify each data instance to one of the labelled classes 211 using a multi-class classification. Initially, the classification module 217 may label the historical data with a labelled class to obtain labelled historical data such that each of the labelled classes 211 corresponds to one training subject. The labelled historical data is used to train the multi-class classifier. In an embodiment, one or more anomalies of the plurality of historical spectral data 107 may be identified using Gaussian distribution. Further the data repository 111 may be updated by removing the historical spectral data 107 associated with the one or more anomalies and the labelled class associated with the historical spectral data 107.

In an embodiment, upon classifying each data instance of the spectral data 107 to one of the labelled classes 211, the best model determination module 219 may determine a plurality of best fit models 213 from the plurality of prediction models 113. In an embodiment, the prediction models 113 may be predetermined for each of the training subjects and may be stored in the data repository 111. Further, each prediction model may be obtained as a machine learning regression model trained using reference blood compound concentration values 117 for the historical spectral data 107 associated with the training subject. In an embodiment, the best model determination module 219 may determine a count of data instances of the spectral data 107 assigned with a corresponding labelled class for each labelled class of the plurality of labelled classes 211. Further, the best model determination module 219 may identify one or more labelled classes 211 with the highest count of data instances. Subsequently, the best model determination module 219 may obtain the one or more prediction models 113, corresponding to the one or more identified labelled classes 211 as the one or more best fit models 213.

In an embodiment, the concentration prediction module 221 may be configured to calculate the blood compound concentration values 117 using each of the determined best fit models 213. Further, the concentration prediction module 221 may determine the final blood compound concentration of the test subject by calculating the weighted average of the blood compound concentration values 117.

In an embodiment, the process of predicting the blood compound concentration of the target may be performed in the following steps:

1. Obtaining Prediction Models:

Suppose, if there are 'N' subjects in the training set, then a plurality of prediction models '$\Psi_k$' may be retrieved from the data repository 111, such that 'k' is a value between 1 to N. As an example, the prediction model used may be a Partial Least Squares (PLS) regression model. Further, when there is a test subject which does not belong to the training set, one of the plurality of prediction models '$\Psi_k$' may be assigned to the test subject based on the multi-class classification.

2. Obtaining Best Fit Models for Each of the Plurality of Subjects:

Initially, a multi-class classifier with 'N' classes, each class having a label 'k', such that $k \in \{1, \ldots, N\}$ may be trained using spectral data 107 of $k^{th}$ subject in the training set. Subsequently, a multiclass classification of the test subject data may be performed to select best fit prediction models using the multi-class classifier. Finally, the output of each of the best fit prediction models may be combined to determine the best fit model for the new test subject.

In an embodiment, an N-class classifier may correspond to 'N' subjects in the training set. Further, the labelled data for training the multi-class classifier may be obtained as following:

Consider a spectra data matrix for subject 'k' as $$S^k = \begin{bmatrix} x_1^k & \cdots & \cdots & \cdots & x_{129}^k \\ x_1^{k,1} & \cdots & \cdots & \cdots & x_{129}^{k,1} \\ & & \cdots & & \\ x_1^{k,N} & \cdots & & \cdots & x_{129}^{k,N} \end{bmatrix} = \begin{bmatrix} x_1^k | x_2^k | \cdots \cdots | x_{129}^k \end{bmatrix}$$

Further, the features matrix may be obtained as the transpose of the spectral data matrix $\widehat{S^k}$ as:

$$\widehat{S^k} = \begin{bmatrix} (x_1^k)^T \\ (x_2^k)^T \\ \vdots \\ (x_{129}^k)^T \end{bmatrix}$$

Then, the labelled data set for subject $k=1, 2 \ldots, N$ may be obtained as $[k | \widehat{S^k}]$. Subsequently, the N-class classifier may be trained using the above labelled data.

In an embodiment, the unlabelled data $\widehat{S^t}$ of the test subject consisting of 129 instances of unlabelled data-points may be inputted to the multiclass classifier. Here, $\widehat{S^t}$ may be given as:

$$\widehat{S^t} = \begin{bmatrix} (x_1^t)^T \\ (x_2^t)^T \\ \vdots \\ (x_{129}^t)^T \end{bmatrix}$$

The 129 instances may be predicted by the multi-class classifier to obtain a prediction vector $y_{pred} \in \{1, 2, \ldots, N\}$ with components $y_{pred}[l]$, $l=1, 2 \ldots 129$. In an embodiment, the class with maximum number of predictions may be selected as the first best-class for the test subject. Further, the second best-class may be obtained by selecting the next class with maximum prediction. This process may be continued until a required number of best-classes are obtained.

In an embodiment, the test subject $S_t$ may be assigned the M prediction model $\Psi_{b1}, \Psi_{b2}, \ldots, \Psi_{bM}$ corresponding to the reference subject $S_{b1}, S_{b2}, \ldots, S_{bM}$, such that:

$$b1 = \text{mode}(y_{pred}), b2 = \text{mode}(y_{pred}^{\{b1\}}), b3 = \text{mode}(y_{pred}^{\{b1,b2\}}) \ldots$$

Here, $y_{pred}^{\{b1\}}$ may be the prediction vector with b1 values removed. $y_{pred}^{\{b1,b2\}}$ may be the prediction vector with (b1, b2) values removed. In the current set up, the number of best fit models selected may be 2, i.e., M=2.

3. Prediction of the Blood Compound Concentration:

Some data cleaning procedures may be applied to remove anomalies in the spectral data and outliers in the predicted blood compound values.

In an embodiment, suppose the original labelled data be given by $X^o$, which may be viewed as a horizontal concatenation of glucose array 'g' and the data matrix 'X' as given below:

$$X^o = \begin{bmatrix} g^0 x_0^0 x_1^0 & \cdots & \cdots & x_{129}^0 \\ g^1 x_0^1 x_1^1 & \cdots & \cdots & x_{129}^0 \\ & \cdots & & \\ g^{N-1} x_0^{N-1} x_1^{N-1} & \cdots & \cdots & x_{129}^{N-1} \end{bmatrix} = \begin{bmatrix} g^0 x^0 \\ g^1 x^1 \\ \cdots \\ g^{N-1} x^{N-1} \end{bmatrix} = [g | X]$$

The spectral data X may be used to fit a multivariate Gaussian distribution of the form:

$$\pi_X\left(\mu, \sum\right) = \frac{1}{(2\pi)^{\frac{n}{2}} |\sum|^{\frac{1}{2}}} e^{\left(-\frac{1}{2}(x-\mu)^T \sum^{-1}(x-\mu)\right)}$$

The probabilities for all vectors may be computed using the above distribution to obtain the probabilities p(k) associated with the vectors $x^k$. The vectors corresponding to the lowest probabilities and the corresponding glucose labels may be declared as anomalies and removed.

In an embodiment, combining the outputs from the plurality of best fit models 213 may be performed using the following steps. Initially, in the current setup, two best fit models 213 may be obtained. Further, the best fit models 213 may yield two sets of predictions for the unlabeled data of the test subject. As an example, if $y_1$ is the prediction using the best fit model 213, $\Psi_{b1}$ and $y_2$ is the prediction using the second best fit model $\Psi_{b2}$ then the final prediction may be arrived using weighted averaging as:

$$y = \alpha y_1 + (1-\alpha) y_2$$

As an example, $\alpha$ is set to 0.6 in the current set up.

In an embodiment, an outlier correction procedure may help to improve the prediction accuracy by removing unlikely values in the predicted glucose values. As an example, an outlier may be detected in the predicted glucose vector at index 'k' if:

$$y'_p(k) > \beta * \text{abs}(\text{mean}(y')), \beta \geq 1$$

Here, 'y"' is the first difference of blood compound labels (glucose) in the training set. '$y_p$' is the predicted values and $y'_p(k)$ is the first difference of $y_p$.

Once the outliers are detected in the predicted blood compound (e.g., glucose) vectors, they may be updated with the average of previous and subsequent values in the predicted blood compound vector. Further, the outlier detected at index 'k' in the predicted blood compound vector may be updated as:

$$y'_p(k) = \frac{1}{M} \sum_{l=-M, l \neq k}^{M} y'_p(k-1)$$

As an example, the prediction results obtained based on PLS regression may be as shown in Table 1 below.

TABLE 1

| | | PLS regression | | | |
|---|---|---|---|---|---|
| Training | | | | Best models | No. of |
| subject | R | SEP | MARD | Model 1 Model 2 | anomalies |
| Subject 2 | 0.78 | 283 | 68 | 14 6 | 12 |
| Subject 5 | 0.78 | 302 | 304 | 6 10 | 12 |
| Subject 6 | 0.73 | 321 | 88 | 7 14 | 12 |
| Subject 7 | 0.85 | 88 | 75 | 11 13 | 12 |
| Subject 10 | 0.84 | 122 | 79 | 7 11 | 12 |
| Subject 11 | 0.93 | 163 | 198 | 14 6 | 12 |
| Subject 12 | 0.77 | 318 | 282 | 2 13 | 12 |
| Subject 13 | 0.89 | 89 | 81 | 11 10 | 12 |
| Subject 14 | 0.70 | 366 | 223 | 10 2 | 12 |

Figure 2B:
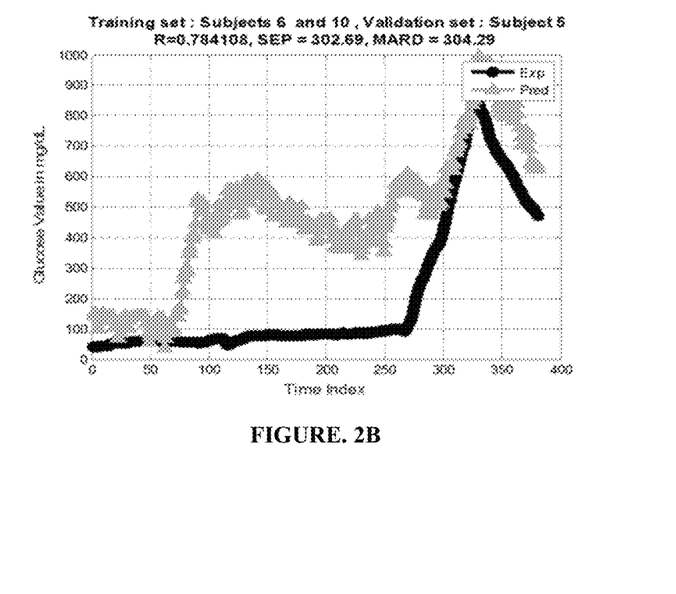
FIGS. 2B and 2C show exemplary prediction results according to an embodiment.
Figure 2C:
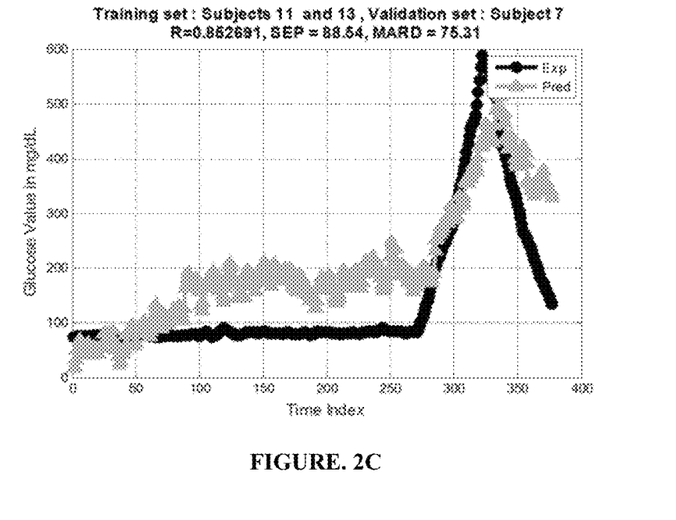

FIGS. 2B and 2C show exemplary prediction results obtained for random subjects—subject 5 and subject 6.

Figure 3:
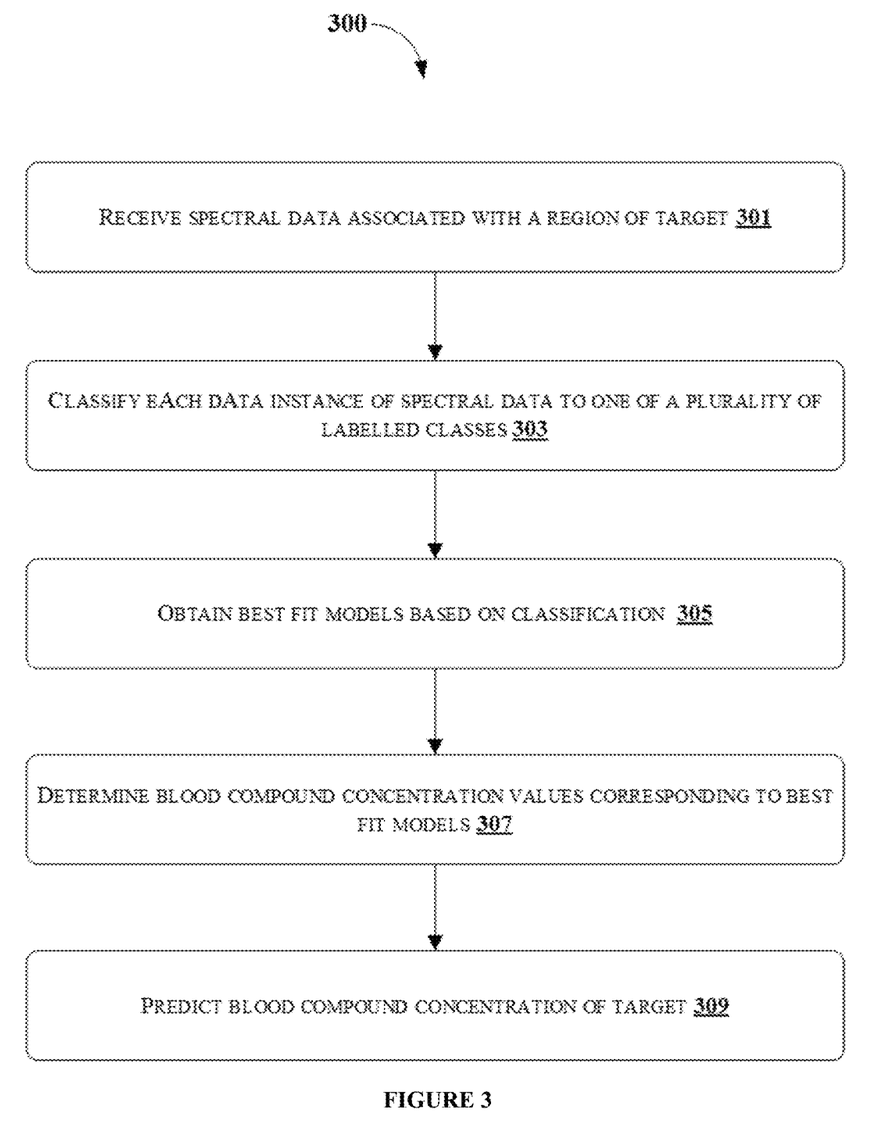
FIG. 3 shows a flowchart illustrating a method of predicting a blood compound concentration of a target according to an embodiment.

FIG. 3 shows a flowchart illustrating a method of predicting a blood compound concentration of a target according to an embodiment.

As illustrated in FIG. 3, the method 300 comprises one or more blocks implemented by the processor 201 for predicting blood compound concentration using a BMS 101. The method 300 may be described in the general context of computer executable instructions. Generally, computer executable instructions can include routines, programs, objects, components, data structures, procedures, modules, and functions, which perform specific functions or implement specific abstract data types.

The order in which the method 300 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 301, the method 300 comprises, receiving, by the BMS 101, spectral data 107 associated with a region of the target. In an embodiment, the spectral data 107 may be collected using an NIR spectroscope associated with the BMS 101. As an example, the spectral data 107 may include, without limitation, a plurality of data instances collected at a plurality of time intervals.

At block 303, the method 300 comprises, classifying, by the BMS 101, each of the plurality of data instances of the spectral data 107 into a plurality of labelled classes 211. In an embodiment, each of the plurality of labelled classes 211 may be predetermined using historical spectral data 107 associated with each of a plurality of training subjects. In an embodiment, each of the plurality of labelled classes 211 may represent one of the plurality of training subjects.

At block 305, the method 300 comprises, obtaining, by the BMS 101, one or more best fit models 213 from a plurality of prediction models 113 based on the classification. In an embodiment, the plurality of prediction models 113 may be models corresponding to the plurality of training subjects. Further, the plurality of prediction models 113 may be obtained as a machine learning regression model trained using reference blood compound concentration values 117 for the historical spectral data 107 associated with the training subject.

At block 307, the method 300 comprises, determining, by the BMS 101, blood compound concentration values 117 corresponding to each of the one or more best fit models 213. In an embodiment, the one or more best fit models 213 may be obtained by performing following actions. Initially, a count of data instances of the spectral data 107 assigned with a corresponding labelled class may be determined for each labelled class of the plurality of labelled classes 211. Subsequently, one or more labelled classes 211 with the highest count of data instances may be identified. Finally, the prediction models 113 corresponding to the one or more labelled classes 211 may be obtained as the one or more best fit models 213.

At block 309, the method 300 comprises, predicting, by the BMS 101, the blood compound concentration of the target using the blood compound concentration values 117 predicted using the best fit models. The BMS 101 may provide the predicted blood compound concentration of the target. For example, the BMS 101 may provide the predicted blood compound concentration of the target for display. As another example, the BMS 101 may transmit the predicted blood compound concentration of the target to another device via a network. As another example, the BMS 101 may provide the predicted blood compound concentration of the target for output via a speaker.

Computer System

Figure 4:
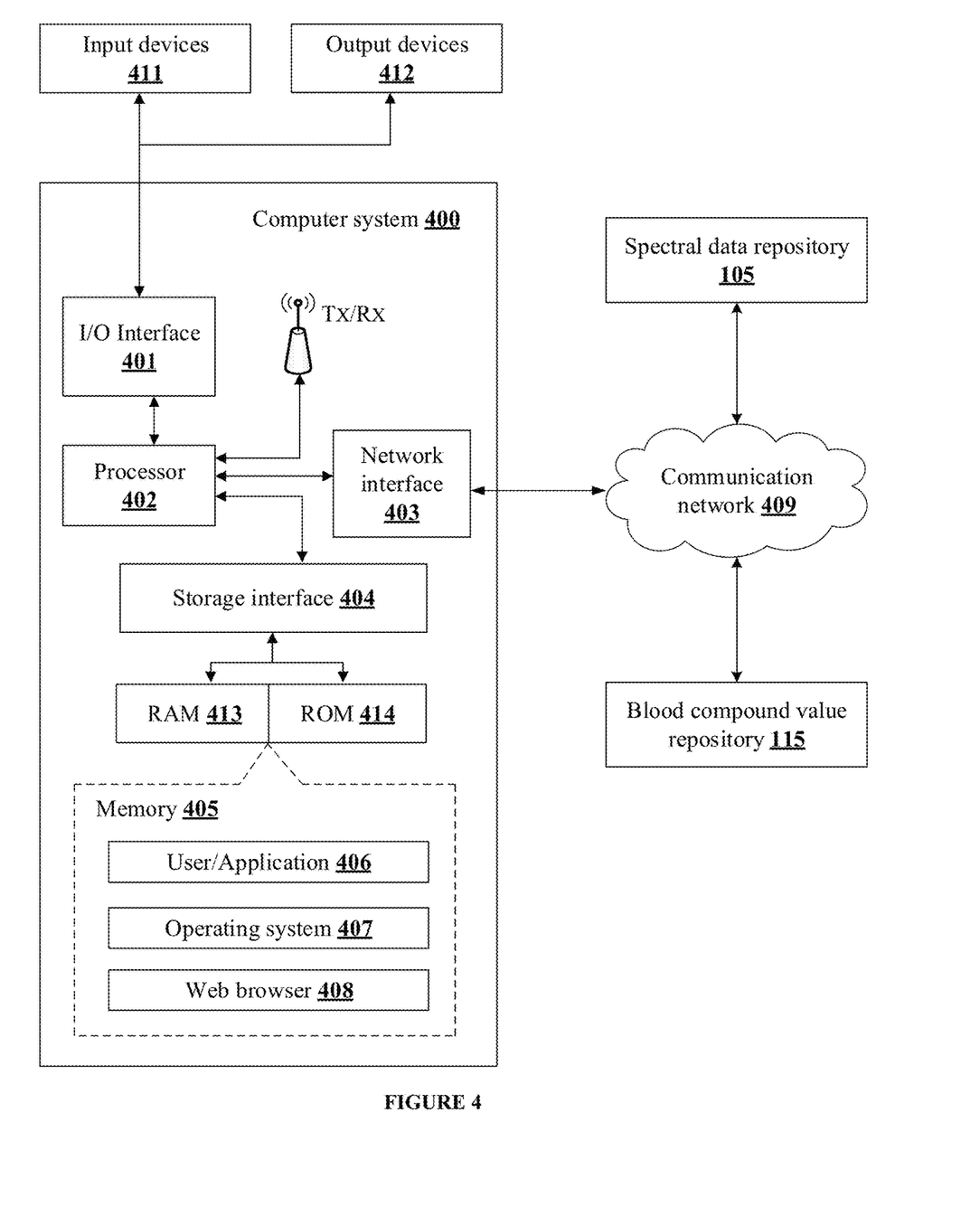
FIG. 4 is a block diagram of an exemplary computer system according to an embodiment.

FIG. 4 illustrates a block diagram of an exemplary computer system 400 for implementing embodiments consistent with the present disclosure. In an embodiment, the computer system 400 may be the BMS 101 illustrated in FIG. 1, which may be used for predicting a blood compound concentration of a target. The computer system 400 may include a central processing unit ("CPU" or "processor") 402. The processor 402 may comprise at least one data processor for executing program components for executing user- or system-generated business processes. A user may include a person, a subject, a caretaker of the subject or any system/sub-system being operated in parallel to the computer system 400. The processor 402 may include specialized processing units such as integrated system (bus) controllers, memory management control units, floating point units, graphics processing units, digital signal processing units, etc.

The processor 402 may be disposed in communication with one or more input/output (I/O) devices (411 and 412) via I/O interface 401. The I/O interface 401 may employ communication protocols/methods such as, without limitation, audio, analog, digital, stereo, IEEE®-1394, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE® 802.n/b/g/n/x, Bluetooth, cellular (e.g., Code-Division Multiple Access (CDMA), High-Speed Packet Access (HSPA+), Global System For Mobile Communications (GSM), Long-Term Evolution (LTE) or the like), etc. Using the I/O interface 401, the computer system 400 may communicate with one or more I/O devices 411 and 412.

In an embodiment, the processor 402 may be disposed in communication with a communication network 409 via a network interface 403. The network interface 403 may communicate with the communication network 409. The network interface 403 may employ connection protocols including, without limitation, direct connect, Ethernet (e.g., twisted pair 10/100/1000 Base T), Transmission Control Protocol/Internet Protocol (TCP/IP), token ring, IEEE® 802.11a/b/g/n/x, etc. Using the network interface 403 and the communication network 409, the computer system 400 may receive historical spectral data 107 from a spectral data repository 105. Further, the network interface 403 may also be used to establish communication with a blood compound value repository 115 for receiving blood compound concentration values 117.

In an implementation, the communication network 409 may be implemented as one of the several types of networks, such as intranet or Local Area Network (LAN) and such within the organization. The communication network 409 may either be a dedicated network or a shared network, which represents an association of several types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the communication network 409 may include a variety of network devices, including routers, bridges, servers, computing devices, storage devices, etc.

In some embodiments, the processor 402 may be disposed in communication with a memory 405 (e.g., RAM 413, ROM 414, etc. as shown in FIG. 4) via a storage interface 404. The storage interface 404 may connect to memory 405 including, without limitation, memory drives, removable disc drives, etc., employing connection protocols such as Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user/application interface 406, an operating system 407, a web browser 408, and the like. In some embodiments, computer system 400 may store user/application data 406, such as the data, variables, records, etc. as described in this disclosure. Such databases may be implemented as fault-tolerant, relational, scalable, secure databases such as Oracle® or Sybase®.

The operating system 407 may facilitate resource management and operation of the computer system 400. Examples of operating systems include, without limitation, APPLE® MACINTOSH® OS X®, UNIX®, UNIX-like system distributions (E.G., BERKELEY SOFTWARE DISTRIBUTION® (BSD), FREEBSD®, NETBSD®, OPENBSD, etc.), LINUX® DISTRIBUTIONS (E.G., RED HAT®, UBUNTU®, KUBUNTU®, etc.), IBM® OS/2®, MICROSOFT® WINDOWS® (XP®, VISTA®/7/8, 10 etc.), APPLE® IOS®, GOOGLE™ ANDROID™, BLACKBERRY® OS, or the like.

The user interface 406 may facilitate display, execution, interaction, manipulation, or operation of program components through textual or graphical facilities. For example, the user interface 406 may provide computer interaction interface elements on a display system operatively connected to the computer system 400, such as cursors, icons, check boxes, menus, scrollers, windows, widgets, and the like. Further, Graphical User Interfaces (GUIs) may be employed, including, without limitation, APPLE® MACINTOSH® operating systems' Aqua IBM® OS/2®, MICROSOFT® WINDOWS® (e.g., Aero, Metro, etc.), web interface libraries (e.g., ActiveX®, JAVA®, JAVASCRIPT®, AJAX, HTML, ADOBE® FLASH etc.), or the like.

The web browser 408 may be a hypertext viewing application. Secure web browsing may be provided using Secure Hypertext Transport Protocol (HTTPS), Secure Sockets Layer (SSL), Transport Layer Security (TLS), and the like. The web browsers 408 may utilize facilities such as AJAX, DHTML, ADOBE® FLASH®, JAVASCRIPT®, JAVA®, Application Programming Interfaces (APIs), and the like. Further, the computer system 400 may implement a mail server stored program component. The mail server may utilize facilities such as ASP, ACTIVEX®, ANSI® C++/C #, MICROSOFT®, .NET, CGI SCRIPTS, JAVA®, JAVASCRIPT®, PERL®, PHP, PYTHON®, WEBOBJECTS etc. The mail server may utilize communication protocols such as Internet Message Access Protocol (IMAP), Messaging Application Programming Interface (MAPI), MICROSOFT® exchange, Post Office Protocol (POP), Simple Mail Transfer Protocol (SMTP), or the like. In some embodiments, the computer system 400 may implement a mail client stored program component. The mail client may be a mail viewing application, such as APPLE® MAIL, MICROSOFT® ENTOURAGE®, MICROSOFT® OUTLOOK®, MOZILLA® THUNDERBIRD®, and the like.

Furthermore, one or more computer-readable storage media may be utilized in implementing embodiments consistent with the disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals. That is, the computer-readable medium may be a non-transitory computer-readable medium. Examples include Random Access Memory (RAM), Read-Only Memory (ROM), volatile memory, non-volatile memory, hard drives, Compact Disc (CD) ROMs, Digital Video Disc (DVDs), flash drives, disks, and any other known physical storage media.

Advantages of the Embodiments of the Present Disclosure are Illustrated Herein.

In an embodiment, the method of present disclosure may be used for accurate prediction of blood compound concentration of a target.

In an embodiment, the method of present disclosure discloses uses subject specific independent prediction models for predicting the blood compound concentration and thus enhances accuracy of the prediction.

The terms "an embodiment", "embodiment", "embodiments", "the embodiment", "the embodiments", "one or more embodiments", "some embodiments", and "one embodiment" mean "one or more (but not all) embodiments of the disclosure" unless expressly specified otherwise.

The terms "including", "comprising", "having" and variations thereof mean "including but not limited to", unless expressly specified otherwise.

The enumerated listing of items does not imply that any or all the items are mutually exclusive, unless expressly specified otherwise. The terms "a", "an" and "the" mean "one or more", unless expressly specified otherwise.

A description of an embodiment with several components in communication with each other does not imply that all such components are required. On the contrary, a variety of optional components are described to illustrate the wide variety of possible embodiments of the disclosure.

When a single device or article is described herein, it will be clear that more than one device/article (whether they cooperate) may be used in place of a single device/article. Similarly, where more than one device or article is described herein (whether they cooperate), it will be clear that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

It is therefore intended that the scope of the disclosure not be limited by this detailed description, but rather by on the claims. Accordingly, the embodiments of the present disclosure are intended to be illustrative, but not limiting, of the scope of the disclosure, which is set forth in the following claims.

REFERENCE NUMERALS

| Reference Number | Description |
|---|---|
| 100 | Environment |
| 101 | Blood compound monitoring system (BMS) |
| 103 | Communication network |
| 105 | Spectral data repository |
| 107 | Historical spectral data |
| 109 | Spectrometer |
| 111 | Data repository |
| 113 | Prediction models |
| 115 | Blood compound value repository |
| 117 | Blood compound concentration values |
| 119 | Blood compound measurement device |
| 201 | Processor |
| 203 | I/O interface |
| 205 | Memory |
| 207 | Data |
| 209 | Modules |
| 211 | Labelled classes |
| 213 | Best fit model |
| 215 | Other data |
| 217 | Classification module |
| 219 | Best model determination module |
| 221 | Concentration prediction module |
| 223 | Other modules |
| 400 | Exemplary computer system |
| 401 | I/O Interface of the exemplary computer system |
| 402 | Processor of the exemplary computer system |
| 403 | Network interface |
| 404 | Storage interface |
| 405 | Memory of the exemplary computer system |
| 406 | User/Application |
| 407 | Operating system |
| 408 | Web browser |
| 409 | Communication network in the exemplary environment |
| 411 | Input devices |
| 412 | Output devices |
| 413 | RAM |
| 414 | ROM |

What is claimed is:

1. A method of predicting a blood compound concentration of a target, the method comprising:

receiving, by one or more processors, spectral data associated with a region of the target, using near-infrared (NIR) spectroscopy, wherein the spectral data comprises a plurality of data instances collected at a plurality of time intervals, and the spectral data corresponds to characteristics of glucose of the target;

classifying, by the one or more processors, each of the plurality of data instances of the spectral data to one of a plurality of labelled classes, wherein each of the plurality of labelled classes is predetermined using a historical spectral data associated with a plurality of training subjects;

obtaining, by the one or more processors, one or more best fit models from a plurality of prediction models based on the classification, wherein the plurality of prediction models are models corresponding to the plurality of training subjects, the plurality of predicting models being obtained as a machine learning regression model trained using reference blood compound concentration values for the historical spectral data associated with the training subjects;

determining, by the one or more processors, blood compound concentration values corresponding to each of the one or more best fit models;

predicting, by the one or more processors, the blood compound concentration of the target using the blood compound concentration values determined using the one or more best fit models;

displaying the predicted blood compound concentration of the target for the target's health monitoring, wherein the obtaining the one or more best fit models comprises:

determining, for each labelled class of the plurality of labelled classes, a count of data instances of the spectral data assigned;

identifying one or more labelled classes with a highest count of data instances; and obtaining the prediction models corresponding to the one or more labelled classes with the highest count of data instances as the one or more best fit models.

2. The method of claim 1, wherein each of the plurality of labelled classes represents one of the plurality of training subjects.

3. A system for predicting a blood compound concentration of a target, the system comprising:

a processor; and a memory communicatively coupled with the processor, wherein the memory stores processor-executable instructions, which when executed by the processor cause the processor to:

receive spectral data associated with a region of the target, using near-infrared (NIR) spectroscopy, wherein the spectral data comprises a plurality of data instances collected at a plurality of time intervals, and the spectral data corresponds to characteristics of glucose of the target;

classify each of the plurality of data instances of the spectral data to one of a plurality of labelled classes, wherein each of the plurality of labelled classes is predetermined using a historical spectral data associated with a plurality of training subjects;

obtain one or more best fit models from a plurality of prediction models based on the classification, wherein the plurality of prediction models are models corresponding to the plurality of training subjects, the plurality of models being obtained as a machine learning regression model trained using reference blood compound concentration values for the historical spectral data associated with the training subjects;

determine blood compound concentration values corresponding to each of the one or more best fit models;

predict the blood compound concentration of the target using the blood compound concentration values determined using the one or more best fit models; and display the predicted blood compound concentration of the target for the target's health monitoring, wherein the processor is configured to obtain one or more best fit models by:

determining, for each labelled class of the plurality of labelled classes, a count of data instances of the spectral data assigned;

identifying one or more labelled classes with highest count of data instances; and obtaining the prediction models corresponding to the one or more labelled classes with the highest count of data instances as the one or more best fit models.

4. The system of claim 3, wherein each of the plurality of labelled classes represents one of the plurality of training subjects.

5. A method comprising:

receiving spectral data associated with a subject, wherein the spectral data corresponds to characteristics of glucose of the subject;

classifying the spectral data using a plurality of classes;

determining a respective number of data instances of the spectral data corresponding to each class of the plurality of classes;

determining classes, of the plurality of classes, that include a highest number of data instances, obtaining a set of best fit models based on classifying the spectral data;

determining blood compound concentration values corresponding to the set of best fit models;

predicting a blood compound concentration value of the subject, based on the determined blood compound concentration values corresponding to the set of best fit models; and displaying the predicted blood compound concentration of the target for the target's health monitoring, wherein the obtaining the set of best fit models comprises obtaining the set of best fit models from a set of prediction models, where the set of best fit models is based on the classes that include a highest number of data instances, wherein the set of prediction models correspond to a plurality of training subjects, wherein the set of prediction models includes a machine learning regression model trained using reference blood compound concentration values for historical spectral data associated with a training subject.

6. The method of claim 5, wherein the spectral data is received using near-infrared (NIR) spectroscopy.

7. The method of claim 5, wherein the spectral data includes a plurality of data instances collected at a plurality of time intervals.

8. The method of claim 5, wherein the plurality of classes is predetermined using historical spectral data associated with a plurality of training subjects.

* * * * *